United States Patent [19]

Chimenti et al.

[11] Patent Number: 5,419,185
[45] Date of Patent: May 30, 1995

[54] OPTIMIZATION OF THE PROCESS TO MANUFACTURE DEWAXED OIL

[75] Inventors: Robert J. L. Chimenti, Short Hills; Gerald M. Halpern, Bridgewater, both of N.J.

[73] Assignee: Exxon Research and Engineering Company, Florham Park, N.J.

[21] Appl. No.: 195,794

[22] Filed: Feb. 10, 1994

[51] Int. Cl.⁶ .................... G01N 31/08; G01V 9/04
[52] U.S. Cl. .................... 73/54.01; 356/70; 356/432; 250/256
[58] Field of Search ............... 73/54.01, 54.02, 54.08; 356/70, 39, 432, 434, 436; 250/256

[56] References Cited

U.S. PATENT DOCUMENTS

| | | | |
|---|---|---|---|
| 4,113,384 | 9/1978 | Lauer et al. | 356/70 |
| 4,880,748 | 11/1989 | Altman et al. | 356/70 |
| 5,114,860 | 5/1992 | Hayashi | 436/69 |
| 5,121,337 | 6/1992 | Brown | 364/498 |
| 5,194,910 | 3/1993 | Kirkpatrick, Jr. et al. | 356/70 |
| 5,266,800 | 11/1993 | Mullins | 250/256 |
| 5,298,224 | 3/1994 | Plum | 356/39 |

FOREIGN PATENT DOCUMENTS 883074627 2/1989 European Pat. Off. .

Primary Examiner—Hezron E. Williams
Assistant Examiner—J. David Wiggins
Attorney, Agent, or Firm—Ronald D. Hantman

[57] ABSTRACT

Method and apparatus for optimizing the extraction of aromatics from waxy distillates and the dewaxing of waxy raffinates in the manufacture of lubricating oils.

12 Claims, 6 Drawing Sheets

OPTIMIZATION OF THE PROCESS TO MANUFACTURE DEWAXED OIL

BACKGROUND OF THE INVENTION

The present invention relates to determining the viscosity index of dewaxed oil from the optical absorption spectrum of the waxy raffinate used to manufacture the oil. This allows the optimization of the manufacturing steps to produce the dewaxed oil.

The Viscosity Index (VI) of a lube basestock is a measure of its change in viscosity with temperature. The smaller the change in viscosity with temperature the higher is its VI. A high VI is desirable in oils for severe service, such as motor and aviation lubes, since they must provide equally good lubrication over the range from cold starting to high operating temperature conditions.

Solvent extraction of aromatics present in the distillate is a key step in the manufacture of lube oils. The presence of aromatic compounds cause the lube oil to exhibit a relatively large change in its viscosity with changes in temperature. The amount of aromatics to be extracted depends upon the increase in the VI that is required to meet the product specifications for the particular viscosity grade.

Solvent extraction is a physical separation process that uses a solvent, N-methylpyrollidone (NMP), for example, to preferentially dissolve and remove the aromatic compounds. This process also reduces the Conradson carbon and sulfur contents of the distillate thereby having the additional beneficial effects of improving oxidation stability and color of the finished basestocks.

Following solvent extraction, the waxy raffinate may be hydrofined in a catalytic fixed bed process involving the addition of hydrogen to remove sulfur and nitrogen-containing molecules and to partially saturate hydrocarbon molecules. This process further improves the stability and color of the oils.

Finally, the hydrofined waxy raffinate is solvent-dewaxed in order to remove enough wax for the pour point of the dewaxed oil to be lowered to meet specification for the particular viscosity grade. The removal of normal paraffin molecules which constitute a large fraction of the wax decreases the Viscosity Index of the basestock.

Optimization of the extraction and dewaxing processes to meet the VI and pour point specifications and maximize dewaxed oil yield represents a challenge to the lube oil manufacturer. Refinery laboratory analysis of the waxy raffinate is typically carried out in order to provide information to the process operator on the required increase in VI. The analysis comprises the steps of simulating the dewaxing process in the lab to obtain a sample of the dewaxed raffinate, measuring the viscosity at 40° C. and 100° C., calculating the VI from the viscosities obtained at these two temperatures, and the pour or solids point of the dewaxed oil, and finally the correction of the VI which depends upon the measured pour or solids points. If the final VI of the laboratory-dewaxed oil differs from the target VI, the process operator will increase or decrease the extraction severity to increase or decrease, respectively, the VI.

A problem with this procedure is that there is a time delay of, typically, 8–18 hours, from the time a change is made in extractor severity or a feed change to the time that a lab dewaxed oil VI is available. Consequently, considerable amounts of off-spec oil or VI-give away may have occurred. In addition, if a change to the extractor is made, this time-delay for a lab measurement precludes subsequent adjustments and lab checks on the results. Also, the laboratory work is time-consuming and the measurements require skilled personnel.

The utility of our invention is that it can provide the process operator with an accurate and precise estimate of the VI of the dewaxed oil from a rapid, simple measurement on the waxy raffinate. The method may be implemented in an on-line analyzer or refinery lab procedure.

SUMMARY OF THE INVENTION

The present invention includes a method to determine the viscosity index of dewaxed oil used to make lube basestocks manufactured from distillates. The method includes the steps of irradiating the waxy raffinate with radiation within the frequency range between 3500 and 12000 $cm^{-1}$, measuring the absorption spectrum within the frequency range, and converting the absorption spectrum into a number representative of the Viscosity Index (VI) of the lube basestock.

The invention also includes a method for optimizing the Viscosity Index (VI) of dewaxed oil manufactured from a waxy distillate. This method includes the steps of extracting aromatics from the waxy distillate to produce a waxy raffinate, dewaxing the waxy raffinate to produce a dewaxed oil, irradiating the waxy raffinate with radiation within the frequency range between 3500 and 12000 $cm^{-1}$, measuring the absorption spectrum within the frequency range, converting the absorption spectrum into a number representative of the viscosity index of the dewaxed oil, and reducing or increasing the aromatics extraction severity in order to approach a VI target.

DESCRIPTION OF PREFERRED EMBODIMENT

Figure 1:
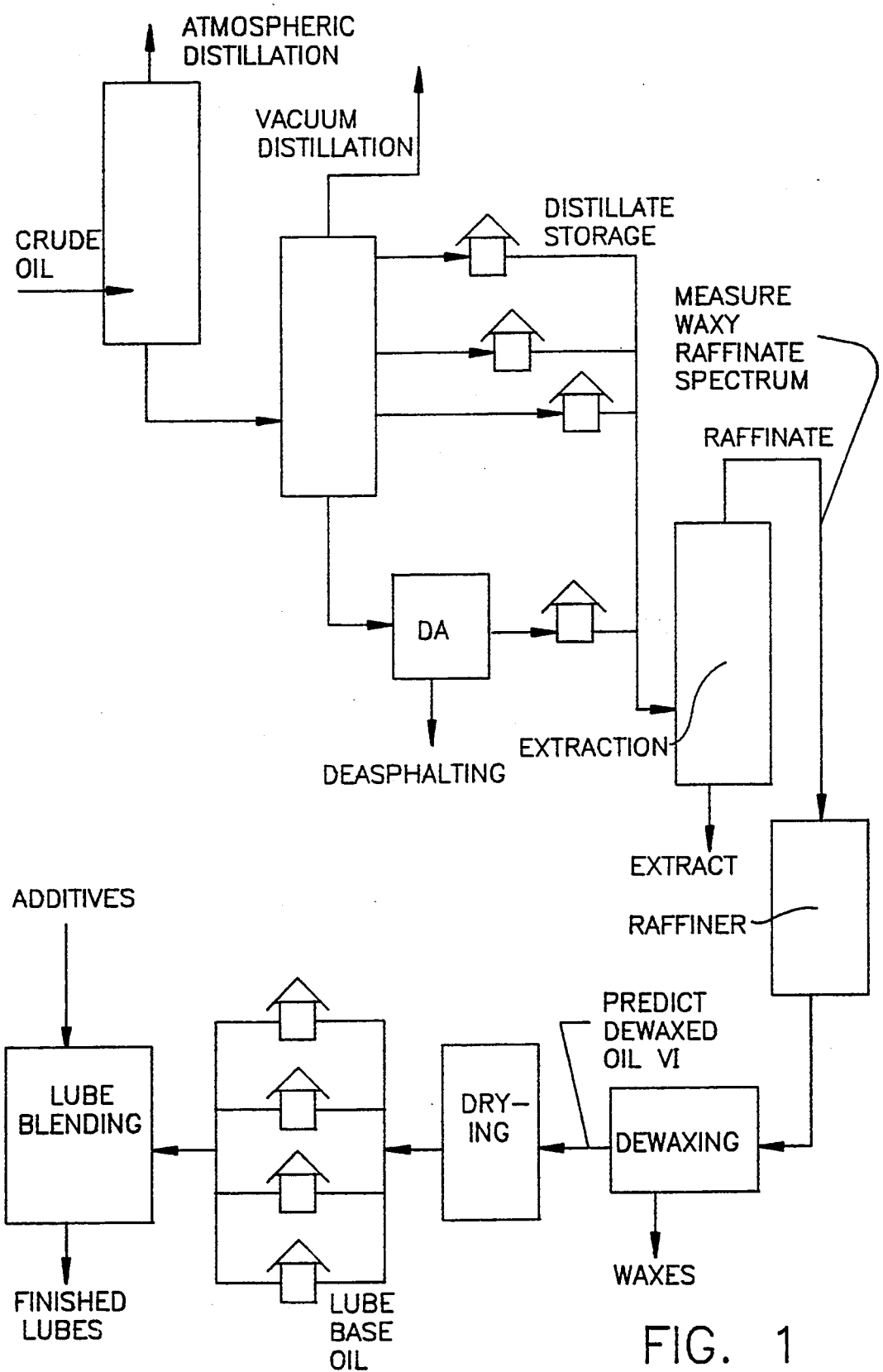
FIG. 1 shows a schematic diagram of the manufacturing process of lube basestocks from crude oil.

FIG. 1 shows a schematic diagram for the production of lube basestocks starting from crude oil. The crude oil is distilled, aromatics are extracted, the waxy raffinate is dewaxed, and the dewaxed oil is used to provide lube basestock. Hydrofining may be carried out before or after dewaxing. The present invention is a means to determine the Viscosity Index of the dewaxed oil from the optical absorption spectrum of the waxy raffinate and to optimize the extraction and dewaxing steps of the manufacturing process of the dewaxed oil from the waxy distillate.

In a preferred embodiment, the invention includes the steps of measuring the optical absorbance spectrum of the waxy raffinate in the spectral frequency range of 6000–9000 cm$^{-1}$ and of utilizing the absorbances in mathematical models that estimate the VI of the dewaxed oil for different viscosity grades. Mathematical models such as multilinear regression and principal components regression have been successfully employed. Other modeling techniques known to those skilled in the art, such as partial least squares and neural networks, could also be applied.

Further features of the method include means to determine from the waxy raffinate spectra, when feed changes to the extractor break-through to the raffinate, means to determine if the spectrum is representative of the sample population as determined by previous measurements, and means to predict other important process and product parameters, such as % wax, % saturates, and viscosities.

EXAMPLE

Table 1 shows a description of 42 samples of 600N vis grade waxy raffinates and the properties of the corresponding dewaxed oils. These were obtained from at least 15 crudes or crude mixtures. The dewaxed oil properties cover a wide range of variation in VI, viscosity, and pour points. For this viscosity grade, the plant target is about 95 VI units at a −9° C. pour point.

Although this example used 600N vis grade, the invention is equally applicable to other vis grades such as 100N.

TABLE 1
600N SAMPLES INCLUDED IN THE EXAMPLE

| CRUDE/CRUDE MIX | DWO VI @ −9 C. | DWO VIS (CS) @ 40 C. | DWO POUR POINT DEGREE C. |
|---|---|---|---|
| ASSAY SAMPLES | | | |
| Sample 1 | 89.9 | 131.15 | −14 |
| Sample 2 | 89.5 | 154.13 | −15 |
| Sample 3 | 79.8 | 188.77 | −15 |
| Sample 4 | 101.8 | 113.75 | −12 |
| Sample 5 | 98.4 | 124.94 | −13 |
| Sample 6 | 92.9 | 140.12 | −13 |
| Sample 7 | 104.6 | 104.7 | −9 |
| Sample 8 | 96.5 | 114.85 | −13 |
| Sample 9 | 104.2 | 108.78 | −12 |
| Sample 10 | 84.2 | 166.26 | −14 |
| Sample 11 | 90.0 | 155.75 | −16 |
| Sample 12 | 74.7 | 121.29 | −17 |
| Sample 13 | 89.9 | 151.21 | −15 |
| Sample 14 | 106.5 | 83.39 | −10 |
| Sample 15 | 84.1 | 101.57 | −16 |
| EXTRACTION SAMPLES | | | |
| Sample 16 | 92.9 | 129.81 | −12 |
| Sample 17 | 95.2 | 120.70 | −10 |
| Sample 18 | 97.7 | 114.83 | −10 |
| Sample 19 | 96.6 | 112.21 | −12 |
| Sample 20 | 98.8 | 106.05 | −10 |
| Sample 21 | 102.2 | 98.95 | −9 |
| Sample 22 | 94.6 | 121.62 | −13 |
| Sample 23 | 97.1 | 106.29 | −12 |
| Sample 24 | 100.3 | 113.06 | −11 |
| Sample 25 | 92.8 | 141.84 | −12 |
| Sample 26 | 96.1 | 130.43 | −11 |
| Sample 27 | 98.7 | 123.49 | −11 |
| Sample 28 | 94.9 | 111.41 | −13 |
| Sample 29 | 96.6 | 105.59 | −10 |
| Sample 30 | 100.0 | 99.97 | −11 |
| PLANT SAMPLES* | | | |
| Sample 31 | 94.8 | 154.8 | −21 |
| Sample 32 | 94.5 | 144.4 | −11 |
| Sample 33 | 93.7 | 142.3 | −6 |
| Sample 34 | 95.7 | 133.0 | −11 |
| Sample 35 | 94.4 | 147.1 | −16 |
| Sample 36 | 93.6 | 154.4 | −16 |
| Sample 37 | 93.4 | 149.4 | −12 |
| Sample 38 | 96.6 | 143.8 | −14 |
| Sample 39 | 93.5 | 151.7 | −13 |
| Sample 40 | 95.1 | 152.1 | −18 |
| Sample 41 | 94.8 | 144.3 | −15 |
| Sample 42 | 95.5 | 143.6 | −15 |

*Mixture of ARAB LT, A960, Olmeca plus minor amounts (<1%) of 8 others

Figure 2:
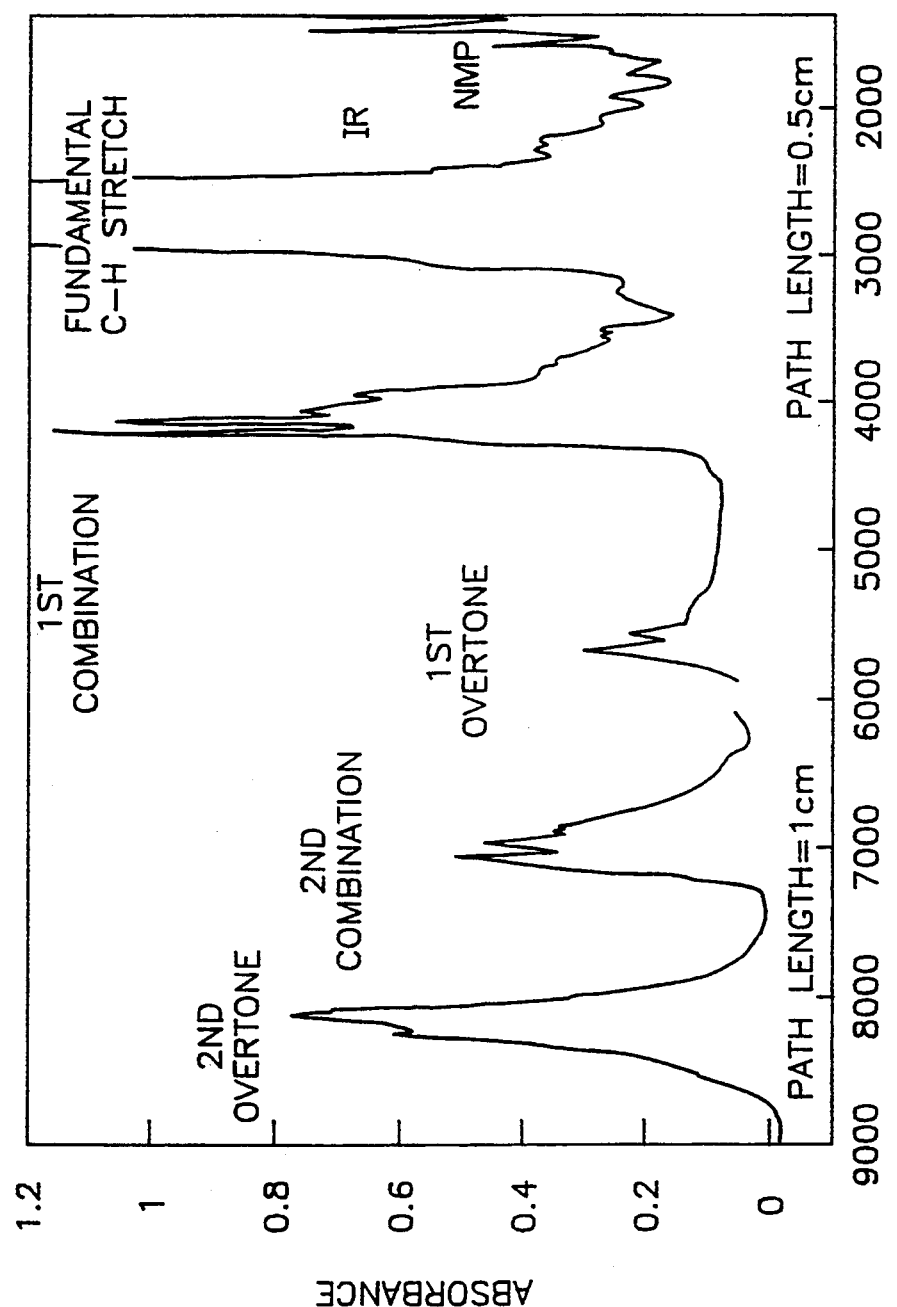
FIG. 2 shows the composite spectra of the samples in Table 1.

FIG. 2 shows composite spectra of the 42 samples in the 6000–9000 cm$^{-1}$ region and for samples 16–30 in the 1500–6000 cm$^{-1}$ region. The spectra were taken with the sample cell heated to 65° C. to ensure that there was only a single homogenous phase and that all of the wax was molten. The optical path length was 1.0 and 0.05 cm for the high and low frequency regions, respectively. All of the measurements were made neat, without sample dilution.

The absorption bands that are seen in the region from 3500–9000 cm$^{-1}$ are overtones and combination bands of the fundamental stretching and bending vibrations of the C—H bonds. The fundamental C—H stretching and bending bands occur near 3000 and 1500 cm$^{-1}$ in the mid-IR and are outside of the linear range of the instrument when measured in a 0.05 cm path length.

Multilinear and Principal Components regression models were developed for each of the 5 bands shown in FIG. 2 using the waxy raffinate absorbance per centimeter path length at each measured spectral frequency as the independent variables, and the dewaxed oil VI as the dependent variable. The standard error of prediction was used as a measure of the model quality and to determine which and how many of the absorbance variables to include in the model. Multilinear regression (MLR) using 3 frequencies in the 6000–9000 cm$^{-1}$ region gave a good model. Three suitable frequencies are about 6100, 7100 and 8100 cm$^{-1}$. An overall error of estimate of 0.94 VI units was obtained by the model.

Figure 3:
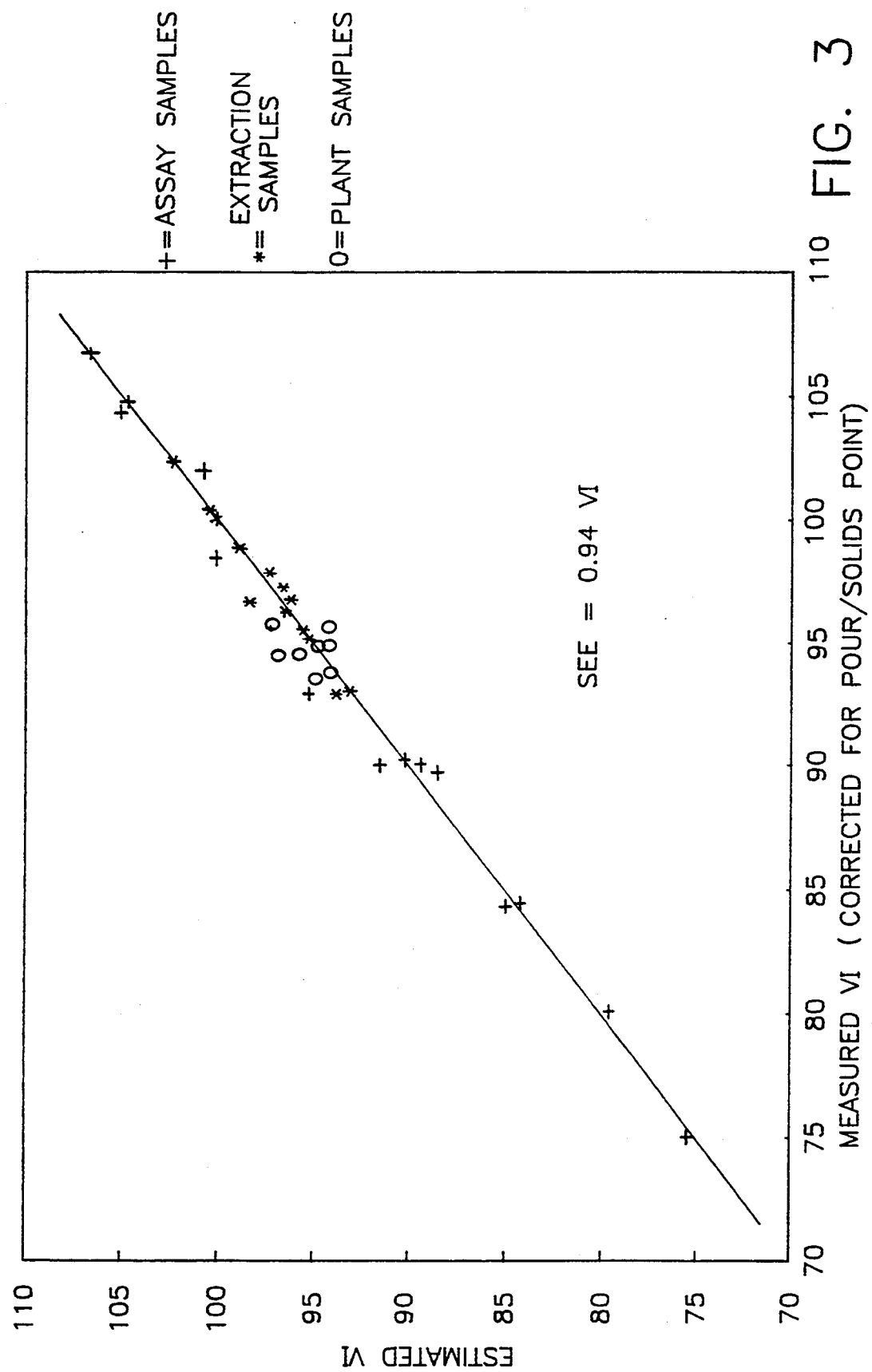
FIG. 3 shows a parity plot of the viscosity index determined by direct measurement and by the present invention.
Figure 4:
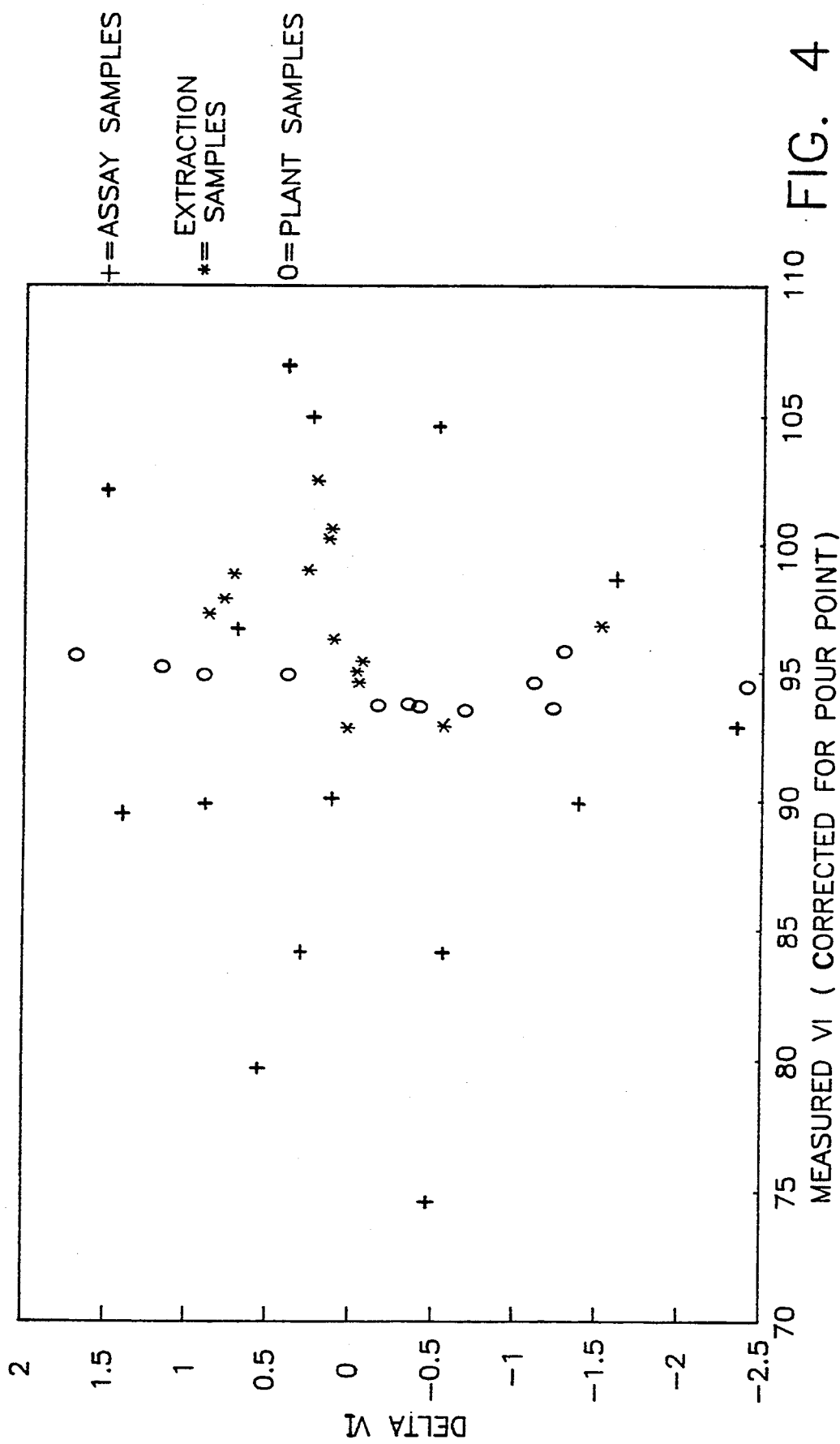
FIG. 4 shows a graph of the residual error (of VI estimate) as a function of dewaxed oil viscosity index.
Figure 5:
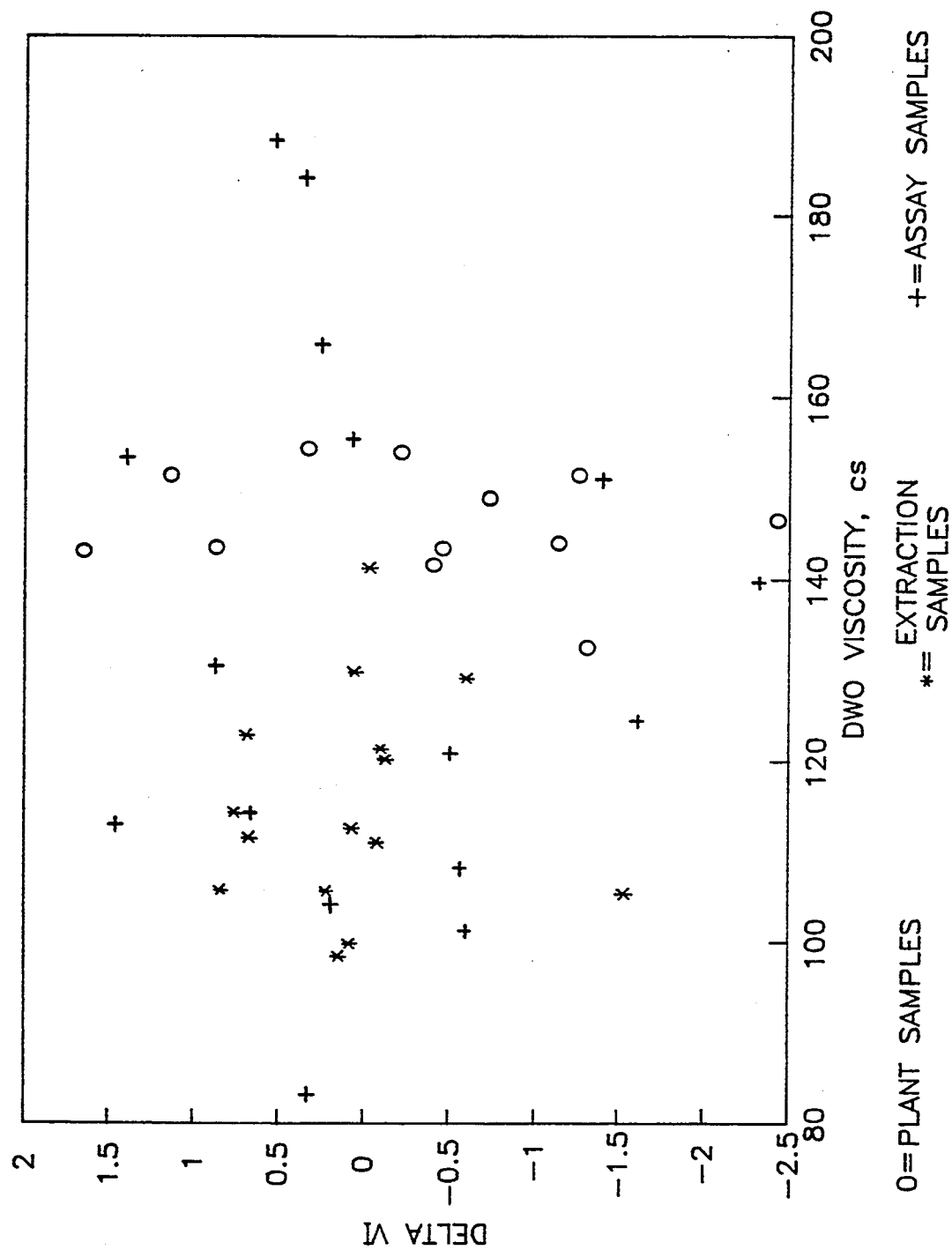
FIG. 5 shows a graph of the residual errors (of viscosity estimate) as a function of dewaxed oil viscosity.
Figure 6:
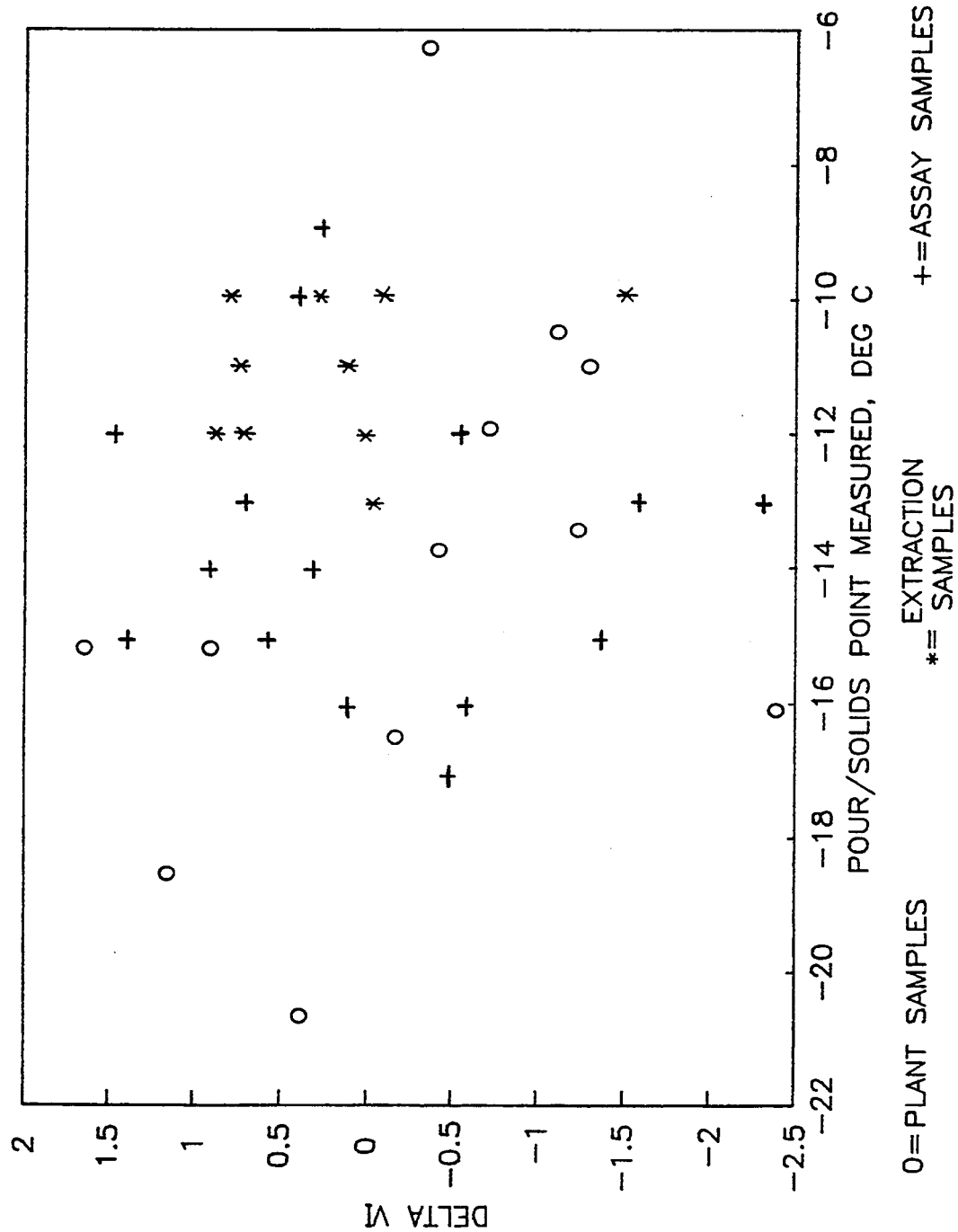
FIG. 6 shows a graph of the residual error as a function of dewaxed oil pour point.

A parity plot of the measured VI, corrected to a common −9° C. pour point, versus the estimated VI from the MLR model for the 42 samples is shown in FIG. 3. The residual errors of estimate are independent of VI, viscosity, and pour point, as shown in FIGS. 4, 5, and 6, respectively. These show, along with the insensitivity of the model to crude source, that the model is sufficiently robust to estimate VI for 600N vis grade lube oils, and distinguish such from the waxy raffinate.

What is claimed is:

1. A method to determine the Viscosity index of dewaxed oil, manufactured from a distillate to produce a waxy raffinate, dewaxing the waxy raffinate to make dewaxed oil and used to make lube basestocks, which is comprising the steps of:
   (a) irradiating the waxy raffinate with light radiation within the frequency range between 3500 and 12000 cm$^{-1}$,
   (b) measuring the absorption spectrum within said frequency range,
   (c) converting said absorption spectrum into a number representative of the Viscosity Index of said dewaxed oil used to make lube basestock 2. The method of claim 1 wherein said frequency range is between 6000 and 9000 cm$^{-1}$.

3. The method of claim 1 wherein said converting step is performed by multilinear regression.

4. The method of claim 1 wherein said converting step is performed by principal components regression.

5. The method of claim 1 wherein said frequency range includes three frequencies between 6000 and 9000 cm$^{-1}$.

6. A method for optimizing the viscosity index of dewaxed oil comprising the steps of:
   (a) extracting aromatics from a waxy distillate to produce a waxy raffinate,
   (b) dewaxing said waxy raffinate to produce a dewaxed oil,
   (c) irradiating the waxy raffinate with radiation within the frequency range between 3500 and 12000 cm$^{-1}$,
   (d) measuring the absorption spectrum within said frequency range,
   (e) converting said absorption spectrum into a number representative of the Viscosity Index of said dewaxed oil,
   (f) changing the operating parameters of said extraction and/or said dewaxing step so as to optimize said Viscosity Index.

7. The method of claim 6 wherein said frequency range is between 6000 and 9000 cm$^{-1}$.

8. The method of claim 6 wherein said converting step is performed by multilinear regression.

9. The method of claim 6 wherein said converting step is performed by principal components regression.

10. The method of claim 6 wherein frequency range includes three frequencies between 6000 and 9000 cm$^{-1}$.

11. A system for optimizing the viscosity index of dewaxed oil comprising the steps of:
    (a) means for extracting aromatics from a waxy distillate to produce a waxy raffinate,
    (b) means for dewaxing said waxy raffinate to produce a dewaxed oil,
    (c) means for irradiating the waxy raffinate with radiation within the frequency range between 3500 and 12000 cm$^{-1}$
    (d) means for measuring the absorption spectrum within said frequency range,
    (e) means for converting said absorption spectrum into a number representative of the Viscosity Index of said dewaxed oil,
    (f) means for changing the operating parameters of said extraction and/or said dewaxing step so as to optimize said viscosity index.

12. The system of claim 11 wherein said frequency range is between 6000 and 9000 cm$^{-1}$.

* * * * *